United States Patent
Hellhammer et al.

(10) Patent No.: US 9,150,987 B2
(45) Date of Patent: *Oct. 6, 2015

(54) AREAL IMPLANT

(75) Inventors: Brigitte Hellhammer, Quickborn (DE); Bernhard Hinsch, Hamburg (DE); Jörg Priewe, Kie (DE); Barbara Schuldt-Hempe, Bad Bramstedt (DE); Christoph Walther, Kattendorf (DE)

(73) Assignee: Ethicon, Inc., Somerville, NJ (US)

( * ) Notice: Subject to any disclaimer, the term of this patent is extended or adjusted under 35 U.S.C. 154(b) by 2517 days.

This patent is subject to a terminal disclaimer.

(21) Appl. No.: 10/477,580

(22) PCT Filed: Mar. 27, 2002

(86) PCT No.: PCT/EP02/03460
§ 371 (c)(1),
(2), (4) Date: Nov. 12, 2003

(87) PCT Pub. No.: WO02/091950
PCT Pub. Date: Nov. 21, 2002

(65) Prior Publication Data
US 2005/0027368 A1   Feb. 3, 2005

(30) Foreign Application Priority Data
May 17, 2001  (DE) .................. 101 23 934

(51) Int. Cl.
*A61F 2/00* (2006.01)
*D04B 21/16* (2006.01)
*A61B 19/00* (2006.01)

(52) U.S. Cl.
CPC ............. *D04B 21/16* (2013.01); *A61F 2/0063* (2013.01); *A61B 2019/5437* (2013.01)

(58) Field of Classification Search
CPC ....................... A61F 2/0063; A61F 2002/0068
USPC ............................................. 606/151
See application file for complete search history.

(56) References Cited

U.S. PATENT DOCUMENTS

| | | | |
|---|---|---|---|
| 5,100,422 A | 3/1992 | Berguer et al. | |
| 5,236,447 A * | 8/1993 | Kubo et al. | 623/1.13 |
| 5,292,328 A | 3/1994 | Hain et al. | |
| 5,695,525 A * | 12/1997 | Mulhauser et al. | 606/151 |
| 6,162,962 A * | 12/2000 | Hinsch et al. | 623/11.11 |
| 6,174,279 B1 | 1/2001 | Girard | |
| 6,551,356 B2 * | 4/2003 | Rousseau | 623/23.72 |
| 6,575,988 B2 * | 6/2003 | Rousseau | 606/151 |
| 6,592,515 B2 * | 7/2003 | Thierfelder et al. | 600/37 |
| 6,610,006 B1 * | 8/2003 | Amid et al. | 600/37 |
| 6,612,977 B2 * | 9/2003 | Staskin et al. | 600/30 |
| 6,966,918 B1 * | 11/2005 | Schuldt-Hempe et al. | 606/151 |
| 2002/0049504 A1 * | 4/2002 | Barault | 623/23.74 |

FOREIGN PATENT DOCUMENTS

WO  WO 01 15625 A  3/2001

* cited by examiner

Primary Examiner — Katherine M Shi
Assistant Examiner — Michael Mendoza
(74) Attorney, Agent, or Firm — Roberts Mlotkowski Safran & Cole, PC (57) ABSTRACT

An areal implant comprises a flexible, porous basic structure which is non-resorbable or partly resorbable and which contains non-resorbable colored elements arranged in a stripe-like pattern. Furthermore, resorbable colored elements arranged in a stripe-like pattern are provided.

15 Claims, 5 Drawing Sheets

Information relating to embodiment A

| Warp design for embodiment A | | | | |
|---|---|---|---|---|
| Thread system I | X | X | Y | Y |
| Thread system II | X | | Y | |
| Thread system III | | X | | Y |

X = uncoloured material
Y = coloured material

| Pattern rapport for embodiment A | | |
|---|---|---|
| Thread system I | Thread system II | Thread system III |
| 2 | 0 | 6 |
| 0 | 4 | 2 |
| | 2 | 4 |
| | 4 | 2 |
| | 2 | 4 |
| | 6 | 0 |
| | 2 | 4 |
| | 4 | 2 |
| | 2 | 4 |
| | 4 | 2 |

Figs. 1A-1D Information relating to embodiment A

| Warp design for embodiment A | | | | |
|---|---|---|---|---|
| Thread system I | X | X | Y | Y |
| Thread system II | X | | Y | |
| Thread system III | | X | | Y |

X = uncoloured material
Y = coloured material

Fig. 1A

| Pattern rapport for embodiment A | | |
|---|---|---|
| Thread system I | Thread system II | Thread system III |
| 2 | 0 | 6 |
| 0 | 4/2 | 2/4 |
|  | 4/2 | 2/4 |
|  | 6/2 | 0/4 |
|  | 4/2 | 2/4 |
|  | 4 | 2 |

Fig. 1B

| Technical data and sketch for embodiment A | | | |
|---|---|---|---|
| Stitches/cm: | 15 | Unit weight – complete mesh (g/m²): | 55 |
| Pore size (mm): | 4.5 | Unit weight – non-resorbable portion (g/m²): | 27 |
| | | Remaining dye portion (g/m²): | 0.074 |

Figs. 2A-2D Information relating to embodiment B

Warp design for embodiment B

| Thread system I | Y | Y | Y | Y | Y | Y | X | X |
|---|---|---|---|---|---|---|---|---|
| Thread system II | Y |  | Y |  | Y |  | X |  |
| Thread system III |  | Y |  | Y |  | Y |  | X |

Fig. 2A

X = uncoloured material
Y = coloured material

Pattern rapport for embodiment B

| Thread system I | Thread system II | Thread system III |
|---|---|---|
| 2 | 0 | 6 |
| 0 | 4 | 2 |
|  | 2 | 4 |
|  | 4 | 2 |
|  | 2 | 4 |
|  | 6 | 0 |
|  | 2 | 4 |
|  | 4 | 2 |
|  | 2 | 4 |
|  | 4 | 2 |

Fig. 2B

Technical data and sketch for embodiment B

| Stitches/cm: | 15 | Unit weight – complete mesh (g/m$^2$): | 55 |
|---|---|---|---|
| Pore size (mm): | 4.5 | Unit weight – non-resorbable portion (g/m$^2$): | 27 |
|  |  | Remaining dye portion (g/m$^2$): | 0.111 |

Figs. 3A-3C  Information relating to embodiment C

| Warp design for embodiment C | | | | | | | | | | | | |
|---|---|---|---|---|---|---|---|---|---|---|---|---|
| Thread system I | X |  | X |  | X |  | Y |  | Y |  | Y |  |
| Thread system II |  | X |  | X |  | X |  | Y |  | Y |  | Y |

Fig. 3A

X = uncoloured material
Y = coloured material

| Pattern rapport for embodiment C | |
|---|---|
| Thread system I | Thread system II |
| 4 | 2 |
| 6 | 0 |
| 2 | 4 |
| 0 | 6 |

Fig. 3B

| Technical data for embodiment C | | | |
|---|---|---|---|
| Stitches/cm: | 6.9 | Unit weight – complete mesh (g/m$^2$): | 92 |
| Pore size (mm): | 1.5 | Unit weight – non-resorbable portion (g/m$^2$): | 30.7 |
|  |  | Remaining dye portion (g/m$^2$): | 0.0844 |

Fig. 3C

Figs. 4A-4C Information relating to embodiment D

| Warp design for embodiment D | | | | | | | | | | | | |
|---|---|---|---|---|---|---|---|---|---|---|---|---|
| Thread system I | Y | | X | | X | | X | | X | | X | |
| Thread system II | | Y | | X | | X | | X | | X | | X |
| Thread system III | Z | | | | | | | | | | | |
| Thread system IV | | Z | | | | | | | | | | |

Fig. 4A

X = uncoloured material
Y = coloured material
Z = coloured material

| Pattern rapport for embodiment D | | | |
|---|---|---|---|
| Thread system I | Thread system II | Thread system III | Thread system IV |
| 4 | 2 | 4 | 2 |
| 6 | 0 | 6 | 0 |
| 2 | 4 | 2 | 4 |
| 0 | 6 | 0 | 6 |

Fig. 4B

| Technical data for embodiment D | | | |
|---|---|---|---|
| Stitches/cm: | 6.9 | Unit weight – complete mesh (g/m$^2$): | 162.2 |
| Pore size (mm): | 1.5 | Unit weight – non-resorbable portion (g/m$^2$): | 25.8 |
| | | Remaining dye portion (g/m$^2$): | 0.02412 |

Fig. 4C

Figs. 5A-5C Information relating to embodiment E

Fig. 5A

| Warp design for embodiment E | | | | | | | | |
|---|---|---|---|---|---|---|---|---|
| Thread system I | X | X | X | X | X | X | Y | Y |
| Thread system II | X | | X | | X | | Y | |
| Thread system III | | X | | X | | X | | Y |

X = uncoloured material
Y = coloured material

Fig. 5B

| Pattern rapport for embodiment E | | |
|---|---|---|
| Thread system I | Thread system II | Thread system III |
| 2 | 0 | 6 |
| 0 | 4/2 | 2/4 |
| | 4/2 | 2/4 |
| | 6/2 | 0/4 |
| | 4/2 | 2/4 |
| | 4 | 2 |

Fig. 5C

| Technical data for embodiment E | | | |
|---|---|---|---|
| Stitches/cm: | 15 | Unit weight – complete mesh (g/m²): | 65 |
| Pore size (mm): | 4.5 | Unit weight – non-resorbable portion (g/m²): | 35.2 |
| | | Remaining dye portion (g/m²): | 0.035 |

AREAL IMPLANT

CROSS-REFERENCE TO RELATED APPLICATIONS

The present application is the national filing of international application PCT/EP02/03460, which was filed on Mar. 27, 2002, and which claims priority to German application no. 101 23 934.3, which was filed on May 17, 2001.

1. Field of the Invention

The invention relates to an areal implant with a flexible, porous basic structure, which is non-resorbable or partly resorbable. The implant is suitable e.g. for the treatment of pelvic floor defects, for repairing a vaginal prolapse, for repairing inguinal hernias or cicatrical hernias, but also for the treatment of other defects.

2. Background

An areal implant with a mesh-like basic structure and textile reinforcing elements is known from DE 199 42 611. The reinforcing elements can be coloured and form a coarse-meshed grid structure which enables the surgeon to assess a distortion of the implant. The colour preferably remains only temporarily, i.e. it is degraded after the implantation into the patient.

DE 196 13 730 describes an areal implant with a flexible basic structure made from a warp-knitted product made from non-resorbable or very slowly resorbable material and with a resorbable material stiffening the basic structure. The stiffening material can be dyed in order to permit a better visual monitoring of the implant during the surgery. During resorption the colour disappears so that in the longer term no dye remains in the body and therefore no undesired side-effects occur.

A warp-knitted implant mesh made from polypropylene multifilament yarn is disclosed in U.S. Pat. No. 5,292,328. The implant mesh can be provided with a grid pattern by using two yarns of different colours. The pattern enables the correct alignment of the implant mesh to be recognised during the operation.

In the previously known areal implants, the colour pattern is either temporary, so that it helps in the assessment of the correct position of the implant only during implantation, and has disappeared by the time of any later necessary surgery, or the colour remains permanently in the body of the patient, which is not acceptable as regards toxic side-effects.

It is the object of the invention to provide an areal implant which permits a safe judgement of the position and alignment in the body of the patient both during implantation and at later points in time, but which, in the longer term, represents at most a small toxic load.

SUMMARY OF THE INVENTION

The areal implant according to the invention has a flexible, porous basic structure, which is non-resorbable or partly resorbable and which contains non-resorbable coloured elements arranged in a stripe-like pattern. In addition, resorbable coloured elements arranged in a stripe-like pattern are provided.

Before and during the surgery for the insertion of the implant, the non-resorbable coloured elements and the resorbable coloured elements form a clearly visible stripe-like pattern which considerably facilitates the handling of the implant. Thus, e.g., the stripes facilitate a symmetrical and controlled cutting to size of the implant during the preparation for the surgery or the surgery itself. Furthermore, the stripe-like pattern indicates the direction in which the implant is to be inserted. The stripes serve as a guide to where sutures are to be placed and thereby guarantee a symmetrical fixing on both sides of the implant. The visibility of the implant during the surgery is generally improved by the stripe-like pattern.

The non-resorbable coloured elements remaining permanently in the implant facilitate, e.g., the explantation of the implant during any necessary new surgery, as the implant is very clearly distinguished by its colour from the surrounding tissue. As the non-resorbable coloured elements are also arranged in a stripe-like pattern, it is also possible to judge the position or orientation or distorted alignment of the implant at this point in time. Furthermore, the non-resorbable coloured elements allow a better recognition of the implant, if any surgery takes place later in the same area, and thus help to avoid damage to the implant.

The toxic long-term load caused to the patient by dyes is slight, as the resorbable coloured elements are present in the body of the patient for only a limited time. Only the non-resorbable coloured elements remain permanently (or at least for a considerable time). This favourable effect is particularly great if the stripe-like pattern of the resorbable coloured elements has a greater colour intensity than the stripe-like pattern of the basic structure. The amount of colouring matter remaining in the patient permanently or for a considerable time is then small overall, but during the surgery for insertion of the implant, which is particularly important for the overall success of the treatment, the position and alignment of the implant can be easily recognised by the resorbable coloured elements.

In the resorbable coloured elements, the colouring matter used is not position-stable. This means that if a matrix made from a resorbable material, in which the colouring matter (e.g. a dye or a pigment) is embedded, decomposes after the implantation, the colouring matter is released. Depending on the type of the colouring matter, it is degraded in the area of the surgery or after transportation at another point in the body of the patient, or it is discharged after transportation. On the other hand, the colouring matter is position-stable in the non-resorbable coloured elements, e.g. by binding or embedding in a non-resorbable polymer matrix.

The basic structure preferably contains textile material, which is present e.g. in the form of yarns, twisted yarns, monofilaments, multifilaments or narrow ribbons. The resorbable coloured elements preferably contain textile material as well, which is resorbable and at least partly dyed, e.g. in the form of yarns, twisted yarns, monofilaments, multifilaments or narrow ribbons.

The resorbable textile material of the resorbable coloured elements can be worked into the basic structure. In preferred versions of the invention, the basic structure is prepared together with the resorbable coloured elements as a whole with the help of textile techniques, e.g. crocheted, warp-knitted, weft-knitted or woven. In this case, e.g. monofilaments and/or multifilaments made from resorbable and non-resorbable material, in each case coloured in different colours or coloured and uncoloured, can be worked with each other, in order thus to produce the basic structure and the resorbable coloured elements including the stripe-like pattern essentially in one procedure.

Various possibilities are conceivable for the design of the stripe-like pattern. E.g., the stripe-like pattern of the resorbable coloured elements can be arranged parallel, but also transverse, to the stripe-like pattern of the basic structure. While, in the former case, the pattern is a pure stripe pattern, in the latter case, a rhomboid or chequered pattern forms. The width of the individual stripes can also be different.

In an advantageous design of the invention, the implant is stiffened by the resorbable coloured elements and/or by a resorbable portion of the basic structure. In this case, the implant is relatively rigid and hard during the surgery, which improves the handling properties and facilitates the surgery process. After the resorbable portions are resorbed, the remaining implant is soft and very tissue-compatible, which acts against long-term complications.

Preferred non-resorbable materials for the basic structure are polyolefins (preferably polypropylene), polyester, polyamides (preferably polyamide 6 or polyamide 6.6) as well as mixtures of polyvinylidine fluoride and copolymers of vinylidene fluoride and hexafluoropropene. Other materials are also conceivable. In this context, a non-resorbable material is also taken to mean a very slowly resorbable material which is attacked only over the course of many months or years in the body of the patient.

Preferably, the resorbable coloured elements are dyed and contain copolymers of L-lactide and glycolide (preferably in the ratio 10:90 or 95:5), polyglycolide, poly-p-dioxanone, copolymers of glycolide, p-dioxanone and trimethylene carbonate or copolymers of glycolide and ε-caprolactam (preferably in the ratio 75:25) as base material. Other materials are also conceivable. Such resorbable materials are also suitable as materials for a resorbable portion of the basic structure.

In a particularly preferred version, the resorbable coloured elements contain a copolymer of L-lactide and glycolide in the ratio 10:90, which is dyed with 1-hydroxy-4-p-toluidino-antraquinone. Multifilament yarn with these components is marketed by Ethicon under the name "Vicryl, violet". Vicryl is a material which is very quickly wetted by tissue fluids. If a multifilament yarn of the Vicryl, violet type is used in a surgery, this yarn is wetted and penetrated practically straight away by tissue fluids or blood, so that the stripe-like pattern of the resorbable coloured elements appears to be very clear and almost black. In this way, a very strong stripe structure is achieved with a relatively small amount of dye.

Non-resorbable materials such as polypropylene or mixtures of polyvinylidene fluoride and copolymers of vinylidene fluoride and hexafluoropropene are wetted much more slowly by tissue fluids and are not penetrated, so that the visibility of non-resorbable coloured elements which contain such materials and an added or embedded colouring matter depends greatly on the proportion of the colouring matter. The proportion of the colouring matter remaining in the patient permanently or at least for a long time is preferably selected to be as small as possible. The preferred used proportions of colouring matter therefore correspond to the proportions or concentrations of colouring matter normally used in non-resorbable suture material.

Basically, colouring matters such as organic dyes or inorganic dye pigments come into consideration both for the non-resorbable coloured elements and for the resorbable coloured elements, which are e.g. added to a polymer and are optionally bound therein or embedded in a polymer matrix. Fluorescent dyes are also possible. Among the dye pigments, e.g. white pigments such as titanium dioxide and zirconium dioxide or yellow iron pigments are to be emphasized. Pigments which contain an element with a high atomic number are X-ray opaque; the use of such dye pigments therefore permits location of the implant after the surgery using X-ray diagnostic procedures. The use of magnetite (brown) in the resorbable coloured elements leads to a magnetic resonance-active material.

An improved detectability of the implant in the magnetic resonance tomograph (MRT) can also be achieved by embedding or attaching coloured or non-coloured polymers in the form of shaped bodies which contain polymers from the basic structure or the coloured elements. Preferably, balls, perforated balls, small tubes, rods, buttons, discs, clips or knots are attached to the implant, which effects a locally increased amount of material, which leads to an increased magnetic resonance visibility. The shaped bodies preferably have a dimension of at least 0.5 mm in length, width and height and are bonded to the implant in a patterned manner by gluing, stitching or melt fusion. In the preferred coloured polymers, an additionally improved optical visibility results from the increased local amount of dye and the size of the shaped bodies. In the case of shaped bodies of resorbable polymers, an improved time-limited magnetic resonance visibility can be achieved, the length of which results from the resorption time of the polymers.

BRIEF DESCRIPTION OF THE DRAWINGS

The invention is explained further in the following, using embodiments. The figures show in FIGS. 1A-1D provide a schematic representation of information relating to a first embodiment (embodiment A) for the implant according to the invention, FIGS. 2A-2D provide a schematic representation of information relating to a second embodiment (embodiment B) for the implant according to the invention, FIGS. 3A-3C provide a schematic representation of information relating to a third embodiment (embodiment C) for the implant according to the invention, FIGS. 4A-4C provide a schematic representation of information relating to a fourth embodiment (embodiment D) for the implant according to the invention and FIGS. 5A-5C provides a schematic representation of information relating to a fifth embodiment (embodiment E) for the implant according to the invention.

DETAILED DESCRIPTION

Firstly, some examples are shown in Table 1 of resorbable materials to which a dye is added and which are suitable for the resorbable coloured elements of the areal implant according to the invention. In Table 1, along with the resorbable base polymer or copolymer, the associated trade name and the dye used with trade name and colour index number (C.I.) are listed. The listed base materials (without the dye) are also suitable for a partly resorbable component of the basic structure of the implant.

In a similar way, examples are listed in Table 2 of non-resorbable materials with the trade name and details of the dye.

In principle, other dyes can also be used in each case.

The material "Panacryl" is resorbed very slowly and could also be given in Table 2 as "non"-resorbable material.

Four examples are shown in Table 3 of selected material combinations from which, using different thread systems, areal implants with non-resorbable coloured elements and with resorbable coloured elements, which in each case are arranged in a stripe-like pattern, can be produced.

TABLE 1

Resorbable materials with dyes

| Material | Trade name | Dye |
| --- | --- | --- |
| Copolymer of L-lactide/glycolide 10/90 | Vicryl | D & C Violett No. 2 [1-hydroxy-4-p-toluidino-antraquinone] C.I. 60725 |
| Polyglycolide (polyglycolic acid) | Dexon | D & C Green |
| Poly-p-dioxanone | PDS, blue | D & C Blue No. 6 [Indigotin] C.I. 73000 |

TABLE 1-continued

Resorbable materials with dyes

| Material | Trade name | Dye |
|---|---|---|
| Poly-p-dioxanone | PDS, violet | D & C Violet No. 2 [1-hydroxy-4-p-toluidino-antraquinone] C.I. 60725 |
| Copolymer of L-lactide/glycolide 95/5 | Panacryl | D & C Violet No. 2 [1-hydroxy-4-p-toluidino-antraquinone] C.I. 60725 |
| Copolymer of L-lactide/glycolide 10/90 | Vicryl rapid | D & C Violet No. 2 [1-hydroxy-4-p-toluidino-antraquinone] C.I. 60725 |
| Copolymer of glycolide (60%), p-dioxanone (14%) and trimethylene carbonate (26%) | Biosyn | D & C Violet |
| Copolymer of glycolide (75%) and epsiloncaprolactam (25%) | Monocryl | D & C Violet No. 2 [1-hydroxy-4-p-p-toluidino-antraquinone] C.I. 60725 |

TABLE 2

Non-resorbable materials with dyes

| Material | Trade name | Dye |
|---|---|---|
| Polypropylene | Prolene | Copper-phthalocyanine blue C.I. 74160 |
| Mixture of polyvinylidene fluoride and a copolymer of vinylidene fluoride and hexafluoropropene | Pronova | Copper-phthalocyanine blue C.I. 74160 |
| Polyester (PET) | Mersilene/Ethibond | D & C Green No. 6 C.I. 61565 |
| Polyamide 6.6 | Suturamid, black | Indanthrene Direktschwarz R Colloisol, composed ½ each of VAT Blue 20 (C.I. 59800) and olive dye (C.I. 69515)/Palamid Black 00-6005 |
| Polyamide 6/Polyamide 6.6 | Ethilon, black | Hematoxylin |
| Polyamide 6 | Ethilon, blue | Pigment Blue 9860/Chromophtal Blue A3R C.I. Pigment Blue 60 |
| Polyamide 6.6 | Nurolon, black | Logwood extract (hematin), black C.I. 75290 |

TABLE 3

Selected material combinations

| No. | Thread system I | Thread system II | Thread system III | Thread system IV |
|---|---|---|---|---|
| 1 | 60 den polypropylene twisted yarn, uncoloured (X) | Twisted yarn of 60 den polypropylene, uncoloured and 320 den Vicryl, uncoloured (X) | Twisted yarn of 60 den polypropylene, uncoloured and 320 den Vicryl, uncoloured (X) | |
| | 60 den polyproplyene twisted yarn, coloured (Y) | Twisted yarn of 60 den polyproplyene, coloured and 320 den Vicryl, coloured (Y) | Twisted yarn of 60 den polyproplyene, coloured and 320 den Vicryl, coloured (Y) | |
| 2 | 3.5 mil Pronova, uncoloured, monofilament and 320 den Vicryl, uncoloured (X) | 3.5 mil Pronova, uncoloured, monofilament and 320 den Vicryl, uncoloured (X) | 3.5 mil Pronova, uncoloured, monofilament and 320 den Vicryl, uncoloured (X) | |
| | 3.5 mil Pronova, coloured, monofilament and 320 den Vicryl, coloured (Y) | 3.5 mil Pronova, coloured, monofilament and 320 den Vicryl, coloured (Y) | 3.5 mil Pronova, coloured, monofilament and 320 den Vicryl, coloured (Y) | |
| 3 | 3.5 mil Pronova, uncololured, monofilament and 180 den PDS, uncoloured (X) | 3.5 mil Pronova, uncoloured, monofilament and 180 den PDS, uncoloured (X) | | |
| | 3.5 mil Pronova, coloured, monofilament and 180 den PDS, coloured (Y) | 3.5 mil Pronova, coloured, monofilament and 180 den PDS, coloured (Y) | | |

TABLE 3-continued

Selected material combinations

| No. | Thread system I | Thread system II | Thread system III | Thread system IV |
|---|---|---|---|---|
| 4 | 3.5 mil Prolene, uncoloured, monofilament and 320 den Vincryl, uncoloured (X) | 3.5 mil Prolene, uncoloured, monofilament and 320 den Vicryl, uncoloured (X) | 320 den Vicryl, coloured (Z) | 320 den Vicryl, coloured (Z) |
|  | 3.5 mil Prolene, coloured, monofilament and 320 den Vicryl, coloured (Y) | 3.5 mil Prolene, coloured, monofilament and 320 den Vicryl, coloured (Y) | | |

Five embodiments of areal implants are described in the following in a manner familiar to a person skilled in the art with the help of FIGS. 1A-1D, 2A-2D, 3A-3C, 4A-4C and 5A-5C.

For the production of such areal-structured, coloured implant meshes, combinations of coloured and uncoloured twisted yarns or monofilaments are required. Depending on the desired colour intensity of the stripe-like patterns on the implant mesh, multi-stage twisted yarns or monofilaments are selected. In the examples, the material combinations from Table 3 are used.

Embodiment A

Figure 1A:
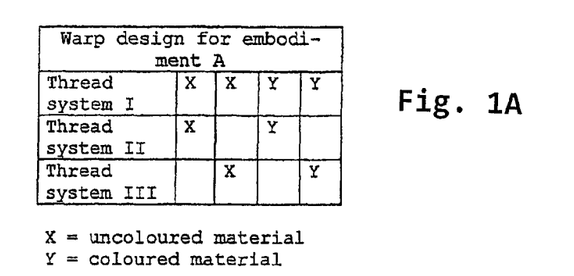
Figure 1B:
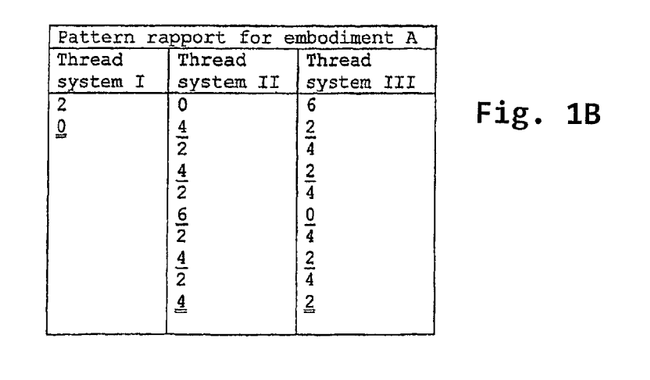
Figure 1C:
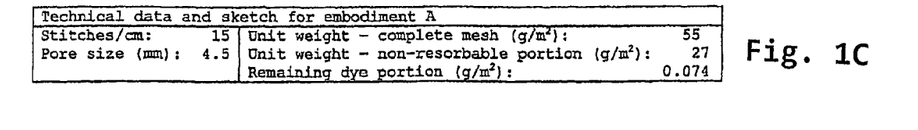

For this embodiment, the material combination No. 1 from Table 3 was selected. The implant was produced on an 8-gauge, Muller "Raschelina RD3MT3" type crochet galloon machine. The warp rapport followed when setting up the warping machine can be seen in FIG. 1A. The threads marked with "X" consist of uncoloured material, and the threads marked with "Y" consist of coloured material. The pattern report for Embodiment A can be found in FIG. 1 B, and technical data for Embodiment A can be found in FIG. 1C.

Figure 1D:
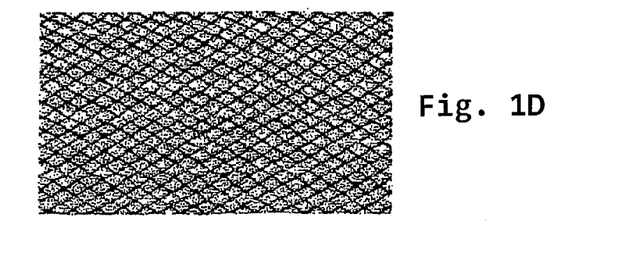

In FIG. 1D, the implant mesh obtained is represented in top view. The dark zones arranged in a stripe-like pattern contain resorbable coloured elements, but also non-resorbable material of the basic structure. After the resorption of the resorbable coloured elements, a stripe-like pattern remains, which is visible in FIG. 1D as bright zones between the dark zones.

Embodiment B

For this embodiment, the material combination No. 1 from Table 3 was selected. The implant was produced on a an 8-gauge, Muller "Raschelina RD3MT3" type crochet galloon machine. The warp rapport followed when setting up the warping machine can be seen in FIG. 2A. The threads marked with "X" consist of uncoloured material, and the threads marked with "Y" consist of coloured material. The pattern report for Embodiment B can be found in FIG. 2B, and technical data for Embodiment B can be found in FIG. 2C.

Figure 2A:
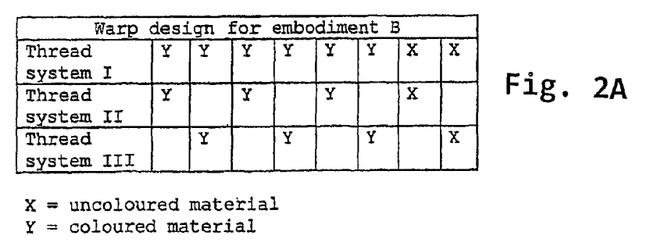
Figure 2B:
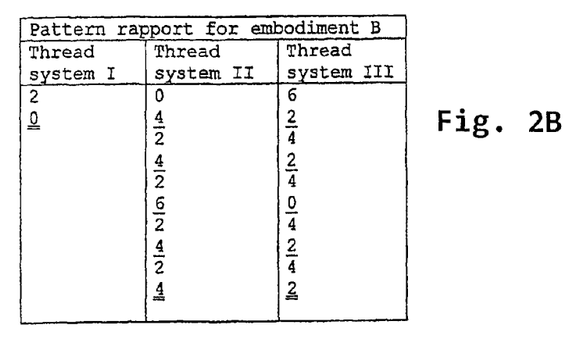
Figure 2C:
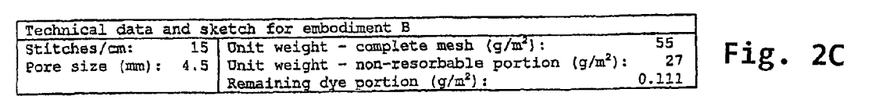
Figure 2D:
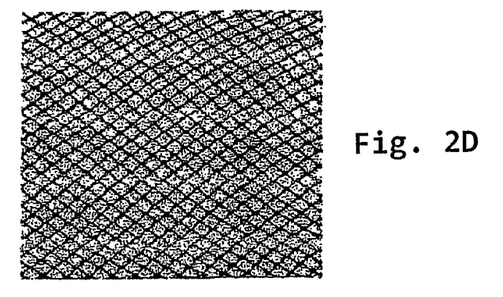
Figure 3A:
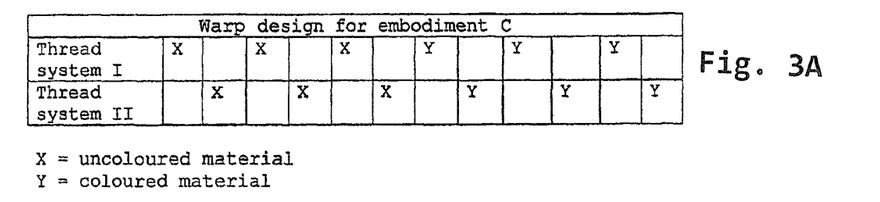
Figure 3B:
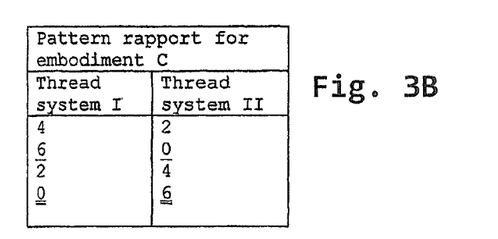
Figure 3C:
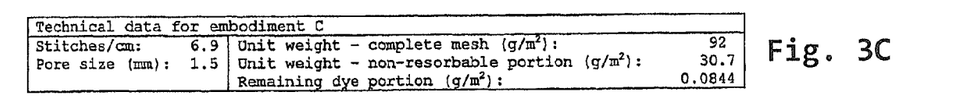
Figure 4A:
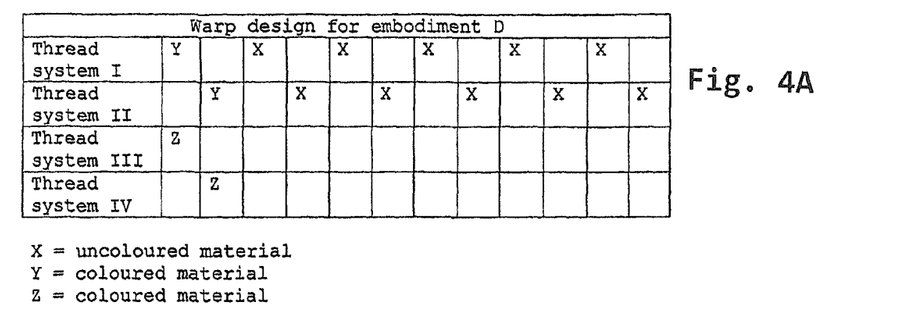
Figure 4B:
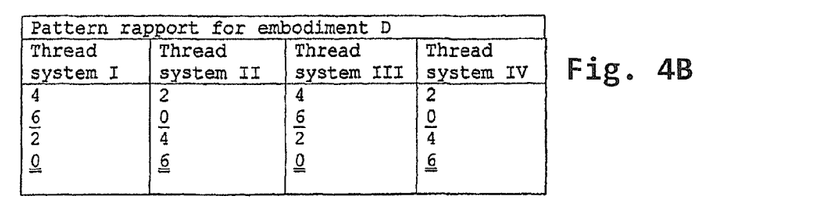
Figure 4C:
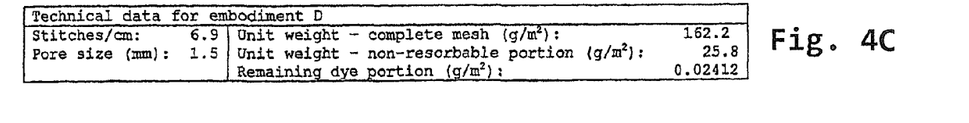
Figure 5A:
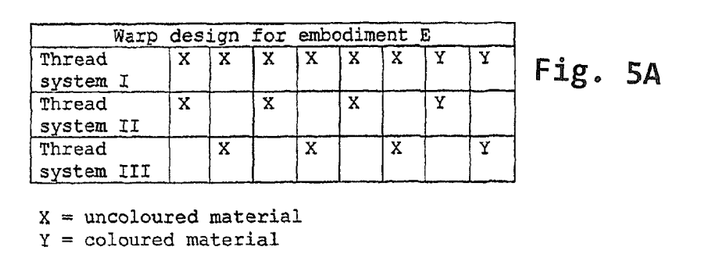
Figure 5B:
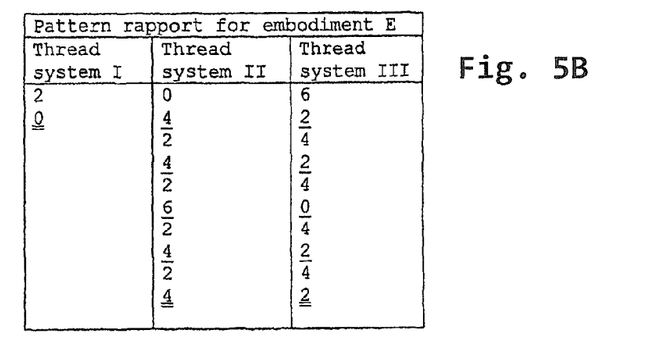
Figure 5C:
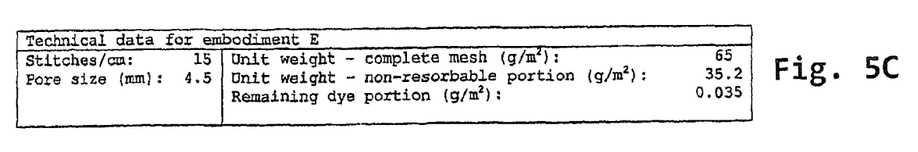

In FIG. 2D, the implant mesh obtained is represented in top view. The dark zones arranged in a stripe-like pattern contain resorbable coloured elements, but also non-resorbable material of the basic structure. After the resorbable coloured elements are resorbed, a stripe-like pattern remains, which is visible in FIG. 2D as bright zones between the dark zones. The dark stripes of the resorbable coloured elements are wider here than in embodiment A.

Embodiment C

For this embodiment, the material combination No. 3 from Table 3 was selected. The implant was produced on a 6-gauge, Mayer raschel machine. The warp rapport followed when setting up the warping machine can be seen in FIG. 3A, in which the other parameters of the implant are also listed in a manner familiar to the person skilled in the art. The threads marked with "X" consist of uncoloured material, and the threads marked with "Y" consist of coloured material. The pattern report for Embodiment C can be found in FIG. 3B, and technical data for Embodiment C can be found in FIG. 3C.

Embodiment D

For this embodiment, the material combination No. 4 from Table 3 was selected. The implant was produced on a 6-gauge, Mayer raschel machine. The warp rapport followed when setting up the warping machine can be seen in FIG. 4A. The threads marked with "X" consist of uncoloured material, and the threads marked with "Y" and with "Z" consist of coloured material. The pattern report for Embodiment D can be found in FIG. 4B, and technical data for Embodiment D can be found in FIG. 4C.

Embodiment E

For this embodiment, the material combination No. 2 from Table 3 was selected. The implant was produced on an 8-gauge, Muller "Raschelina RD3MT3" type crochet galloon machine. The warp rapport followed when setting up the warping machine can be seen in FIG. 5A. The threads marked with "X" consist of uncoloured material and the threads marked with "Y" consist of coloured material. The pattern report for Embodiment E can be found in FIG. 5B, and technical data for Embodiment E can be found in FIG. 5C.

The invention claimed is:

1. An areal implant, comprising:
   a flexible, porous basic structure, which is partly resorbable and which contains non-resorbable colored elements arranged in a stripe-like pattern, and
   resorbable colored elements of a different color, arranged in a stripe-like pattern.

2. The implant according to claim 1, wherein the basic structure contains a textile material which preferably has at least one of the forms selected from the group consisting of yarns, twisted yarns, monofilaments, multifilaments, and narrow ribbons.

3. The implant according to claim 1, wherein the resorbable colored element contains a resorbable textile material which is at least partially dyed, the resorbable textile material preferably having at least one of the forms selected from the group consisting of yarns, twisted yarns, monofilaments, multifilaments, and narrow ribbons.

4. The implant according to claim 3, wherein the resorbable textile material is worked into the basic structure.

5. The implant according to claim 1, wherein the basic structure together with the resorbable colored elements is crocheted, warp-knitted, weft-knitted or woven as a whole.

6. The implant according to claim 1, wherein the stripe-like pattern of the resorbable colored elements is arranged parallel to the stripe-like pattern of the non-resorbable elements.

7. The implant according to claim 1, wherein the stripe-like pattern of the resorbable colored elements is arranged transverse to the stripe-like pattern of the non-resorbable elements.

8. The implant according to claim 1, wherein the stripe-like pattern of the resorbable colored elements has a greater color intensity than the stripe-like pattern of the non-resorbable elements.

9. The implant according to claim 1, wherein the implant is stiffened by the resorbable colored elements and/or by a resorbable portion of the basic structure.

10. The implant according to claim 1, wherein the basic structure contains at least one of a non-resorbable material selected from the group consisting of: polyolefins, polyesters, polyamides, mixtures of polyvinylidene fluoride and copolymers of vinylidene fluoride and hexafluoropropene.

11. The implant according to claim 1, wherein the resorbable colored elements are dyed and contain at least one of a material selected from the group consisting of: copolymers of L-lactide and glycolide, polyglycolide, poly-p-dioxanone, copolymers of glycolide, p-dioxanone and trimethylene carbonate, and copolymers of glycolide and E-caprolactam.

12. The implant according to claim 11, wherein the resorbable colored elements contain a copolymer of L-lactide and glycolide in the ratio 10:90, which is dyed with 1-hydroxy-4-p-toluidino-anthraquinone.

13. The implant according to claim 1, wherein the non-resorbable colored elements contain at least one of the dyes selected from the group consisting of organic dyes, fluorescent dyes, inorganic pigments and magnetite.

14. The implant according to claim 1, wherein the resorbable colored elements contain at least one of the dyes selected from the group consisting of organic dyes, fluorescent dyes, inorganic pigments and magnetite.

15. The implant according to claim 1, wherein resorbable, non-resorbable, colored or uncolored shaped bodies with a dimension of at least 0.5 mm in length, width and height are contained in the implant, wherein the shaped bodies increase the detectability of the implant in a magnetic resonance tomograph (MRT) and consist of substances of the basic structure or of the colored elements.

\* \* \* \* \*